(12) United States Patent
Zhang et al.

(10) Patent No.: US 11,324,847 B2
(45) Date of Patent: May 10, 2022

(54) AUTOMATIC SOURCE-SEEKING INDOOR POLLUTION PURIFYING AND REMOVING DEVICE AND METHOD

(71) Applicant: DALIAN UNIVERSITY OF TECHNOLOGY, Liaoning (CN)

(72) Inventors: Tengfei Zhang, Liaoning (CN); Yun Wei, Liaoning (CN); Shugang Wang, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 17/051,116

(22) PCT Filed: May 28, 2018

(86) PCT No.: PCT/CN2018/088693
§ 371 (c)(1),
(2) Date: Oct. 27, 2020

(87) PCT Pub. No.: WO2019/213998
PCT Pub. Date: Nov. 14, 2019

(65) Prior Publication Data
US 2021/0128769 A1 May 6, 2021

(30) Foreign Application Priority Data

May 7, 2018 (CN) .......................... 201810439998.3

(51) Int. Cl.
*B01D 46/46* (2006.01)
*A61L 9/014* (2006.01)
(Continued)

(52) U.S. Cl.
CPC ................. *A61L 9/014* (2013.01); *A61L 9/20* (2013.01); *B01D 46/0005* (2013.01);
(Continued)

(58) Field of Classification Search
CPC ...... B01D 46/44; B01D 46/442; B01D 46/46; B01D 46/0005
See application file for complete search history.

(56) References Cited

U.S. PATENT DOCUMENTS 8,496,737 B2* 7/2013 Kim .................... B01D 53/72
96/111
8,892,222 B2* 11/2014 Simms ................... B08B 15/04
700/62

FOREIGN PATENT DOCUMENTS

CN      201353577 Y    12/2009
CN      103406326 A    11/2013
(Continued)

OTHER PUBLICATIONS

Wei Y., Zhou H., Zhang T., Wang S., "Inverse identification method of multiple gaseous pollution sources changing with time" Inverse identification of multiple temporal sources releasing the same tracer gaseous pollutant [J]. Building and Environment, Mar. 15, 2017, pp. 184-195, vol. 118.

*Primary Examiner* — Robert A Hopkins
(74) *Attorney, Agent, or Firm* — Muncy, Geissler, Olds & Lowe, P.C.

(57) ABSTRACT

The present invention discloses an automatic source-seeking indoor pollution purifying and removing device and method for airborne pollutants. The device comprises pollutant concentration sensors, a control unit, a position sensor, a power plant, a moving mechanism, a telescopic device, a pollutant collection hood, and a filtering and purifying device. The control unit can identify the actual release positions and hourly release rates of relevant pollutants according to the concentration data monitored by the pollutant concentration sensors, and can control the pollutant collection hood in the device to move to a designated position in a space, so as to realize the collection and (Continued)

removal of pollutants at the release position of the pollutants.

10 Claims, 3 Drawing Sheets

(51) Int. Cl.
*A61L 9/20* (2006.01)
*B01D 46/00* (2022.01)
*B01D 46/42* (2006.01)
*B01D 46/44* (2006.01)
*B01D 53/04* (2006.01)
*B01D 53/30* (2006.01)

(52) U.S. Cl.
CPC ..... *B01D 46/0028* (2013.01); *B01D 46/0036* (2013.01); *B01D 46/4245* (2013.01); *B01D 46/442* (2013.01); *B01D 46/46* (2013.01); *B01D 53/04* (2013.01); *B01D 53/30* (2013.01); *A61L 2209/111* (2013.01); *A61L 2209/12* (2013.01); *A61L 2209/14* (2013.01); *A61L 2209/22* (2013.01); *B01D 2253/102* (2013.01); *B01D 2259/4508* (2013.01); *B01D 2279/50* (2013.01)

(56) References Cited

FOREIGN PATENT DOCUMENTS

| | | |
|---|---|---|
| CN | 203540230 U | 4/2014 |
| CN | 104633877 A | 5/2015 |
| CN | 104776514 A | 7/2015 |
| CN | 106352457 A | 1/2017 |
| CN | 205860224 U | 1/2017 |
| CN | 205860255 U | 1/2017 |
| CN | 106650017 A | 5/2017 |
| CN | 106705255 A | 5/2017 |
| JP | 2013013538 A | 1/2013 |
| KR | 20060027702 A | 3/2006 |

* cited by examiner

AUTOMATIC SOURCE-SEEKING INDOOR POLLUTION PURIFYING AND REMOVING DEVICE AND METHOD

TECHNICAL FIELD

The present invention belongs to the field of indoor pollutant identification technology and air purification, and relates to an automatic source-seeking indoor pollution purifying and removing device and method.

BACKGROUND

Indoor air quality is closely related to the living safety and health of people, and controlling the concentration of pollutants is the key to ensuring good air quality. In order to realize the active control of indoor pollutant concentration, it is urgent to develop an air purifying device. The device shall not only be able to accurately identify the emission source information of indoor pollutants, but also be able to move intelligently to a pollution release position to collect and purify the pollutants.

Most of the existing air purifying devices are devices that are placed in a fixed position or need to be moved manually. For example, a utility model patent with a publication number of CN205860224U designs an automatic indoor pollution purifying device. The device contains a purifying device and a detection box, which can remove multiple kinds of pollutants and automatically purify indoor air; the lower part of the device is provided with four rollers to facilitate manual movement. However, since the device can only complete air purification at a placement position, the device is not suitable for indoor environment with a relatively large space.

In order to solve the above problem, an invention patent with a publication number of CN104633877A provides an intelligent mobile air purifier. The purifier comprises a separate air detection device and a mobile purifying device. The air detection device first detects and analyzes the air quality in a space to be purified, and then sends a walking instruction to the mobile purifying device. The mobile purifying device moves according to the instruction and performs air purification, thereby achieving sufficient detection and purification of the indoor environment. However, the device can only deal with pollution sources at a fixed height, and the patent only generally points out that the air detection device is equipped with a control unit which can analyze air pollution information, but does not include a process of identifying pollution source information.

In order to identify the accurate position of a pollution source, an invention patent with a publication number of CN106650017A proposes a method for identifying multiple pollution sources in urban space using a fixed-position pollutant detector. The patent realizes the identification of multiple pollution sources in the urban space by an adjoint method combined with a probability distribution function. However, the method can only identify pollution sources with a constant release intensity, which limits the actual application scope thereof. In addition, when multiple pollution sources exist in a space, the concentration field needs to be simulated again every time the position of a pollution source is determined, and the multiple pollution sources cannot be identified simultaneously. Therefore, sensor data and computer simulation result data need to be transferred mutually for many times in actual application, which takes a lot of time.

In order to simultaneously identify multiple pollution sources with an emission intensity changing with time, an article "Inverse identification method of multiple gaseous pollution sources changing with time" (Wei Y., Zhou H., Zhang T., Wang S. Inverse identification of multiple temporal sources releasing the same tracer gaseous pollutant [J]. Building and Environment, 2017, 118: 184-195.) proposes a method for identifying multiple pollution sources based on Tikhonov regularization operation. The method is to establish a database containing the position information of potential pollution sources first, so as to construct a response matrix which correlates sensor concentrations with pollution source information; and then use Tikhonov regularization operation to inversely calculate the release rates of all potential pollution sources according to the concentration data actually monitored by sensors, so as to determine the number, positions and hourly release rates of actual pollution sources. The method only requires the concentration data monitored by a small number of sensors to accurately identify the positions and hourly release rates of multiple pollution sources that change dynamically with time, and the identification of multiple pollution sources does not require the simulation of concentration field for multiple times. Therefore, the method can be used to efficiently identify multiple pollution sources in actual indoor environment.

To sum up, most of the current indoor air purifying devices are fixed or need to be operated manually, and can only purify the air in a certain area. Whereas some of the so-called intelligent mobile air purifying devices cannot identify pollution source information yet, and therefore cannot accurately remove pollutants at the position of a pollution source. The present invention designs an automatic source-seeking indoor pollution purifying and removing device that can identify the actual positions and hourly release rates of pollution sources through the concentration data monitored by pollutant concentration sensors, which fills the gap that no air purifying device can accurately locate and efficiently remove pollutant release sources at any position and any height indoors at present.

SUMMARY

In view of the defects of the prior art, the present invention provides an automatic source-seeking indoor pollution purifying and removing device. The device can accurately identify and remove pollution sources, and has strong practicability.

The present invention has the following technical solution:

An automatic source-seeking indoor pollution purifying and removing device, comprising pollutant concentration sensors, a control unit, a position sensor, a power plant, a moving mechanism, a telescopic device, a pollutant collection hood, and a filtering and purifying device; the pollutant concentration sensors are used to monitor the indoor pollutant concentration and transfer the data to the control unit; the control unit is used to identify the actual pollution source information of relevant pollutants according to the concentration data monitored by the pollutant concentration sensors, and issue a movement instruction to the power plant according to a current position signal sent by the position sensor in the device; the pollution source information includes the release positions of pollutants; the power plant is used to move the pollutant collection hood to the positions of identified pollution sources by controlling the moving mechanism and the telescopic device; the pollutants collected by the pollutant collection hood are sucked into the filtering and purifying device through a fan for removal; and the inside of the power plant is provided with power supply equipment to supply power for the moving mechanism, the telescopic device and the fan.

Further, the control unit identifies the actual pollution source information of relevant pollutants according to the positions of potential pollution sources of relevant pollutants in combination with the concentration data monitored by the pollutant concentration sensors; the control unit can also continue to dynamically update the pollution source information according to the concentration data monitored by the pollutant concentration sensors in the process of device movement or pollutant removal, until the pollutant concentrations at the positions of all pollution sources are lower than the corresponding pollutant concentration alarm values; and the pollution source information also includes the hourly release rates of pollution sources.

Further, after identifying pollution sources, the control unit can output the positions and hourly release rates of the pollution sources on a pollution source information display, and arrange a movement track of the device according to the pre-input indoor geometric layout information; the front part of the moving mechanism is provided with an obstacle monitoring sensor which returns a signal to the control unit to correct the movement track when an obstacle is encountered; and the control unit also internally has an automatic return function which enables the device to return to the original position after all pollution sources are removed.

Further, the movement track of the device arranged according to the pre-input indoor geometric layout information is that: when all pollution sources release the same kind of pollutants, the control unit arranges the track according to the hourly release rate of each pollution source from higher to lower, and then issues a movement instruction to the power plant; when multiple kinds of pollutants are released from each pollution source, the control unit sorts according to the distance between each pollution source and the device, selects the shortest track that includes all pollution sources, and then issues an instruction to the power plant.

Further, the pollutant concentration sensors include, but are not limited to, a VOC sensor, a microbial sensor and a particulate sensor to monitor the concentrations of indoor gaseous pollutants, microorganisms, and particulates in real time.

Further, the inside of the control unit is provided with a module for controlling the start and stop of the fan; when the pollutant collection hood moves to the release position where a pollution source is located, the fan starts running; and when the concentrations monitored by all the pollutant concentration sensors are lower than the corresponding pollutant concentration alarm values, the fan stops running.

Further, the moving mechanism is connected with the power supply equipment in the power plant, and can receive the movement instruction issued by the power plant.

Further, the telescopic device comprises a fixed base, gimbals and a multi-section arm; the telescopic device is fixed in the device through the fixed base; the pollutant collection hood is connected with the multi-section arm through the gimbals, the arm closest to the pollutant collection hood is a telescopic sleeve pipe, and the length of the arm can be adjusted to change the position of the pollutant collection hood; and each gimbal is connected with the power supply equipment in the power plant, and can receive the movement instruction issued by the power plant.

Further, the inside of the filtering and purifying device may be provided with a primary filter screen, a high-efficiency filter screen, ultraviolet lamps, activated carbon and an air outlet, so as to purify multiple kinds of pollutants and discharge the purified air through the air outlet.

Further, the principle of pollution source identifying process in the control unit is as follows:

Assuming that n (n≥1) potential pollution sources of the same kind exist in a space, when one pollution source is released separately, the hourly release rate of the pollution source and the distribution of the pollutant concentration in the space satisfy a species transport equation:

$$\frac{\partial(\rho c)}{\partial t} + div(\rho u c) = div[\Gamma grad(c)] + q \tag{1}$$

Wherein $\rho$ is an air density, c is a pollutant concentration in the space, t is time, u is a velocity vector, $\Gamma$ is an effective diffusion coefficient, and q is a time-based release rate of a pollution source. When a flow field is fixed, the concentration monitored by each sensor has a linear relationship with the hourly release rate of a fixed pollution source. In order to identify pollution sources, and taking the method proposed in the article "Inverse identification method of multiple gaseous pollution sources changing with time" (Wei Y., Zhou H., Zhang T., Wang S. Inverse identification of multiple temporal sources releasing the same tracer gaseous pollutant [J]. Building and Environment, 2017, 118: 184-195.) as an example, formula (1) is rewritten as:

$$c_i = A_i q_i \tag{2}$$

Wherein $q_i$ is the hourly release rate of the $i^{th}$ pollution source (i=1, . . . , n), $c_i$ is the concentration vector produced when $q_i$ acts alone, $A_i$ is the response matrix describing the relationship between the $i^{th}$ pollution source and the concentration at the sensor monitoring position when the pollution source is released separately, and the matrix is in the following form:

$$A_i = \begin{bmatrix} F_{t_0,i} & 0 & \cdots & \cdots & \cdots & 0 \\ F_{t_1,i} & F_{t_0,i} & 0 & \cdots & \cdots & 0 \\ \vdots & \ddots & \ddots & \ddots & \ddots & \vdots \\ F_{t_k,i} & F_{t_{k-1},i} & \cdots & F_{t_0,i} & \cdots & 0 \\ \vdots & \ddots & \ddots & \ddots & \ddots & \vdots \\ F_{t_{m-1},i} & F_{t_{m-2},i} & \cdots & F_{t_{m-k},i} & \cdots & F_{t_0,i} \end{bmatrix} \in R^{m \times m} \tag{3}$$

Wherein $F_{t_k,i}$ (k=1, . . . , m) is a concentration response factor, i.e., a concentration response monitored by a sensor at the time t=kΔT (ΔT is the minimum time scale of the concentration that can be monitored by the sensor) when a pollutant is released in pulse form at the position of the $i^{th}$ pollution source, and m is the multiple of the entire monitoring time of the sensor relative to ΔT.

When multiple pollution sources are released simultaneously in the space, the concentration data monitored by the sensor is the sum of the release amounts of the pollution sources at the monitoring position, so:

$$c = \sum_{i=1}^{n} c_i = \sum_{i=1}^{n} A_i q_i \tag{4}$$

Wherein c is the concentration actually monitored by the sensor. Since it is necessary to determine the hourly release rates $q_i$ (i=1, . . . , n) of all potential pollution sources, the concentration data of n sensors are needed to make the number of equations equal to the number of unknowns, i.e., the following matrix is formed:

$$\begin{bmatrix} c^1 \\ \vdots \\ c^j \\ \vdots \\ c^n \end{bmatrix} = \begin{bmatrix} A_1^1 & \cdots & A_i^1 & \cdots & A_n^1 \\ \vdots & \ddots & \vdots & \ddots & \vdots \\ A_1^j & \ddots & A_i^j & \ddots & A_n^j \\ \vdots & \ddots & \vdots & \ddots & \vdots \\ A_1^n & \cdots & A_i^n & \cdots & A_n^n \end{bmatrix} \begin{bmatrix} q_1 \\ \vdots \\ q_i \\ \vdots \\ q_n \end{bmatrix} \quad (5)$$

Wherein the superscripts of the variables in the above formula represent the concentration data monitored by the pollutant concentration sensors at different positions, $c^j$ is the pollutant concentration monitored by the $j^{th}$ sensor (j=1, ..., n), and formula (5) can be further rewritten as:

$$C = AQ \quad (6)$$

Wherein $C=[c^1, \ldots, c^j, \ldots, c^n]^T$, and is composed of the concentration data monitored by each sensor; $Q=[q_1, \ldots, q_i, \ldots, q_n]^T$, and contains the hourly release rates of n potential pollution sources; and A is the first term on the right side of the equal sign in formula (5).

C and A in formula (6) are known; in order to determine Q, the matrix A needs to be inverted; however, because the concentration data monitored by the sensors lags behind the release of the pollution sources, A is an ill-conditioned matrix; therefore, Tikhonov regularization operation is introduced, and the following formula is used to identify the hourly release rates of all potential pollution sources of the same kind:

$$Q = (A^T A + \lambda^2 L^T L)^{-1} (A^T C) \quad (7)$$

Wherein $\lambda$ is a regularization parameter, which can be determined by an L-Curve method (Zhou Hongbiao, Inverse identification of gaseous fixed pollution sources [D]. Dalian University of Technology. 2014.), and the inflection point of the curve of the regularization term $\|LQ\|_2$ changing with the solution error term $\|AQ-C\|_2$ is taken as the value of 1. L is a regularization matrix, and the expression is as follows:

$$L = \begin{bmatrix} 1 & -2 & 1 & 0 & \cdots & \cdots & \cdots & 0 \\ 0 & 1 & -2 & 1 & \ddots & \ddots & \ddots & \vdots \\ \vdots & \ddots & \ddots & \ddots & \ddots & \ddots & \ddots & \vdots \\ \vdots & \ddots & \ddots & 1 & -2 & 1 & \ddots & \vdots \\ \vdots & \ddots & \ddots & \ddots & \ddots & \ddots & \ddots & 0 \\ 0 & \cdots & \cdots & \cdots & 0 & 1 & -2 & 1 \end{bmatrix} \in R^{(mn-2) \times mn} \quad (8)$$

$q_i, \ldots, q_n$ are obtained according to the calculated hourly release rate Q, the positions of the potential pollution sources with a release rate of 0 are excluded, and thus the positions and hourly release rates of actual pollution sources can be determined.

Based on the above calculation principle, a pollution source identifying method comprises the following specific steps:

(1) Pre-inputting indoor geometric layout information and position information of all potential pollution sources (pollution sources that may release a certain kind of pollutants) indoors to the control unit;

(2) Arranging (n-1) sensors that monitor the concentrations of the same kind of pollutants at any different positions in a room according to the number n (n≥1) of potential pollution sources for various kinds of pollutants, and returning the real-time concentration data monitored by each sensor and the sensor installation positions to the control unit;

(3) Obtaining an indoor flow field through numerical simulation by solving Navier-Stokes equations according to the pre-input indoor geometric layout information in the control unit, and on the basis of this flow field, solving a species transport equation through numerical simulation for various kinds of pollutants to obtain a unit pulse response F of all potential pollution sources at the positions of all sensors (i.e., the concentration data monitored by a sensor when a pollutant is released in the form of a unit pulse function at the position of a pollution source);

(4) Using formula (3) and formula (5) to establish a response matrix A related only to the flow field, positions of sensors, and positions of potential pollution sources; and (5) Using formula (7) and formula (8) to calculate Q, so as to obtain the calculated hourly release rates $q_i, \ldots, q_n$ of various potential pollution sources, excluding the positions of the potential pollution sources with a release rate of 0, and determining the positions and hourly release rates of actual pollution sources.

The present invention provides an automatic source-seeking indoor pollution purifying and removing device. Compared with traditional indoor purifying devices, the present invention has the following beneficial effects:

1. The pollution source identifying process in the device only requires the concentration data monitored by a small number of sensors to accurately identify the positions and hourly release rates of multiple pollution sources of multiple kinds of pollutants that change dynamically with time;

2. The device has an automatic source-seeking function, which can accurately remove the pollutants at the positions of identified pollution sources; the moving mechanism, in combination with the telescopic device, can collect the pollution sources at any position in a three-dimensional space, and then pollutants are sucked into the filtering and purifying device through a fan for removal; and therefore, the device solves the problem that existing devices cannot simultaneously identify, conduct automatic source-seeking of and remove indoor pollutants.

In the figures: 1 pollutant collection hood; 2 pollutant concentration sensor; 3 pollution source information display; 4 moving mechanism; 5 gimbal; 6 power plant; 7 fixed base; 8 control unit; 9 telescopic reversing hose; 10 ultraviolet lamp; 11 activated carbon filter screen; 12 centrifugal fan; 13 position sensor; 14 telescopic sleeve pipe; 15 multi-section arm; 16 primary filter screen; 17 high-efficiency filter screen; 18 air outlet.

Figure 2:
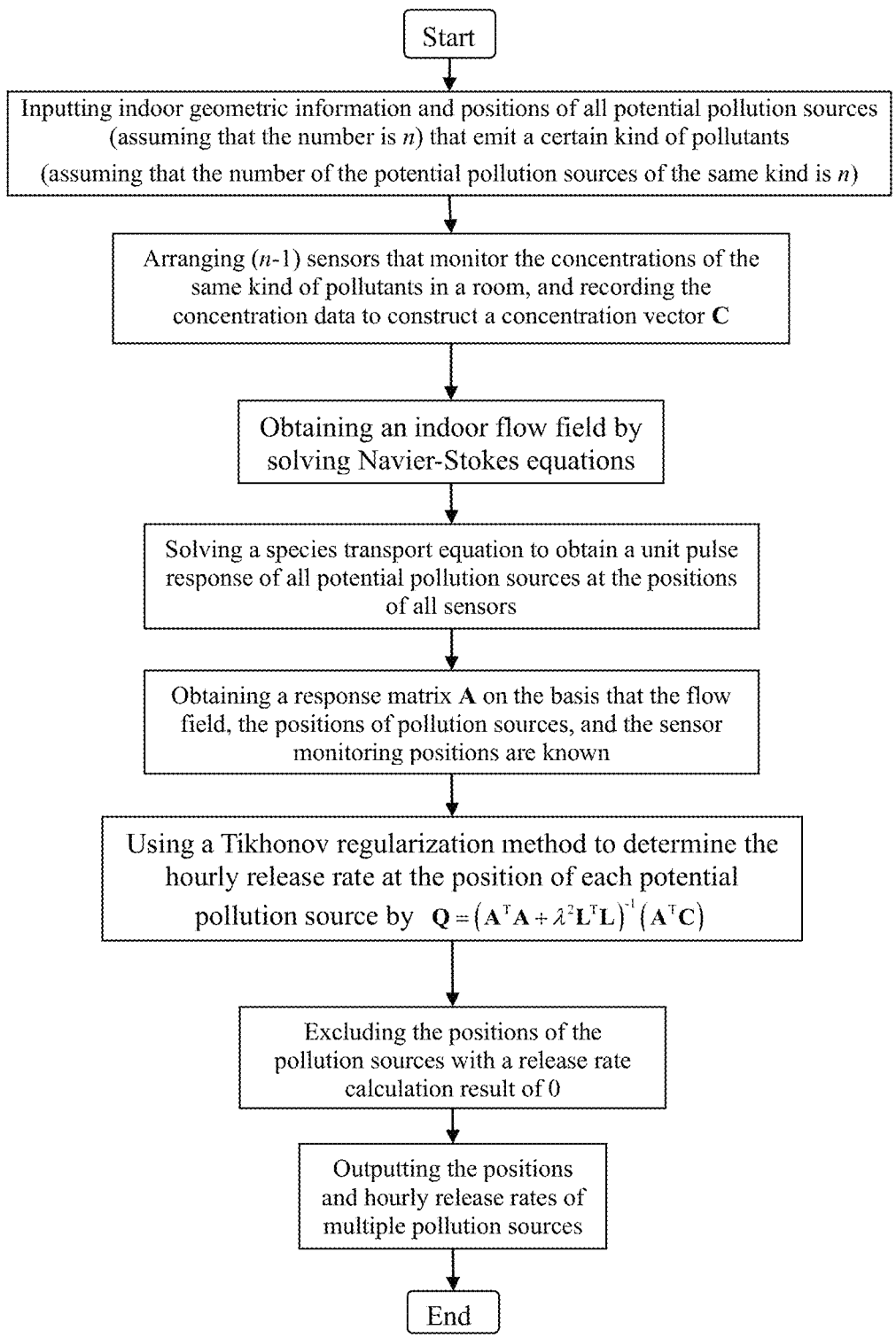

FIG. 2 is a flow chart of identifying positions and release rates of all pollution sources that emit the same kind of pollutants in a control unit of a device. Wherein C is composed of the concentration data monitored by each sensor, i.e., $C=[c^1, \ldots, c^j, \ldots, c^n]^T$; A is a response matrix describing the relationship between pollution sources and sensor-monitored concentrations, which is composed of the unit pulse responses of all potential pollution sources at the positions of all sensors; $\lambda$ is a regularization parameter; and L is a regularization matrix.

Figure 3:
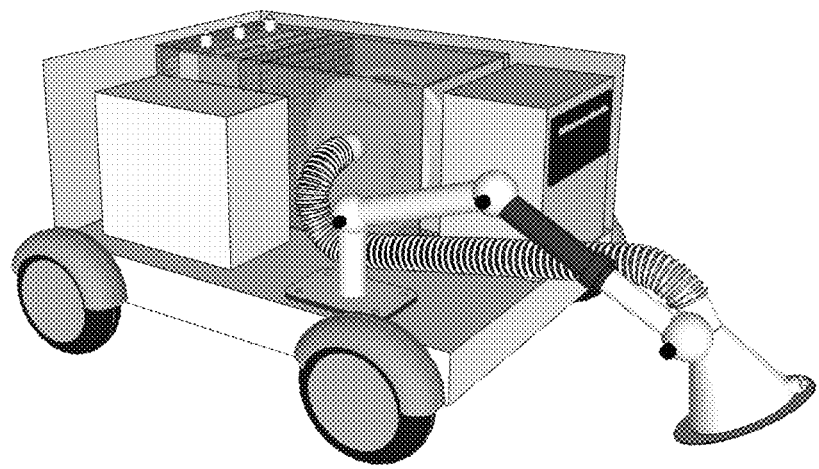

FIG. 3 is an internal schematic diagram of an indoor pollution source intelligent positioning and removing device collecting pollutants at a relatively low pollution source.

Figure 4:
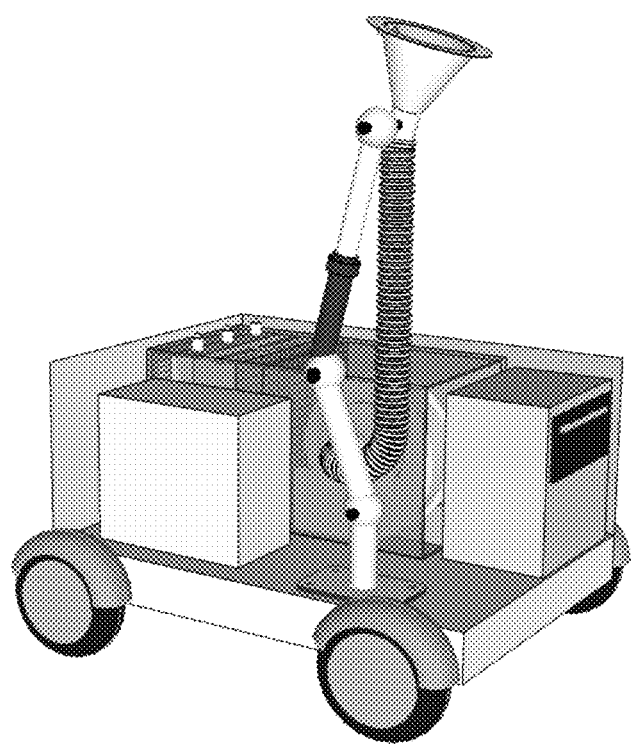

FIG. 4 is an internal schematic diagram of an indoor pollution source intelligent positioning and removing device collecting pollutants at a relatively high pollution source.

DETAILED DESCRIPTION

Figure 1:
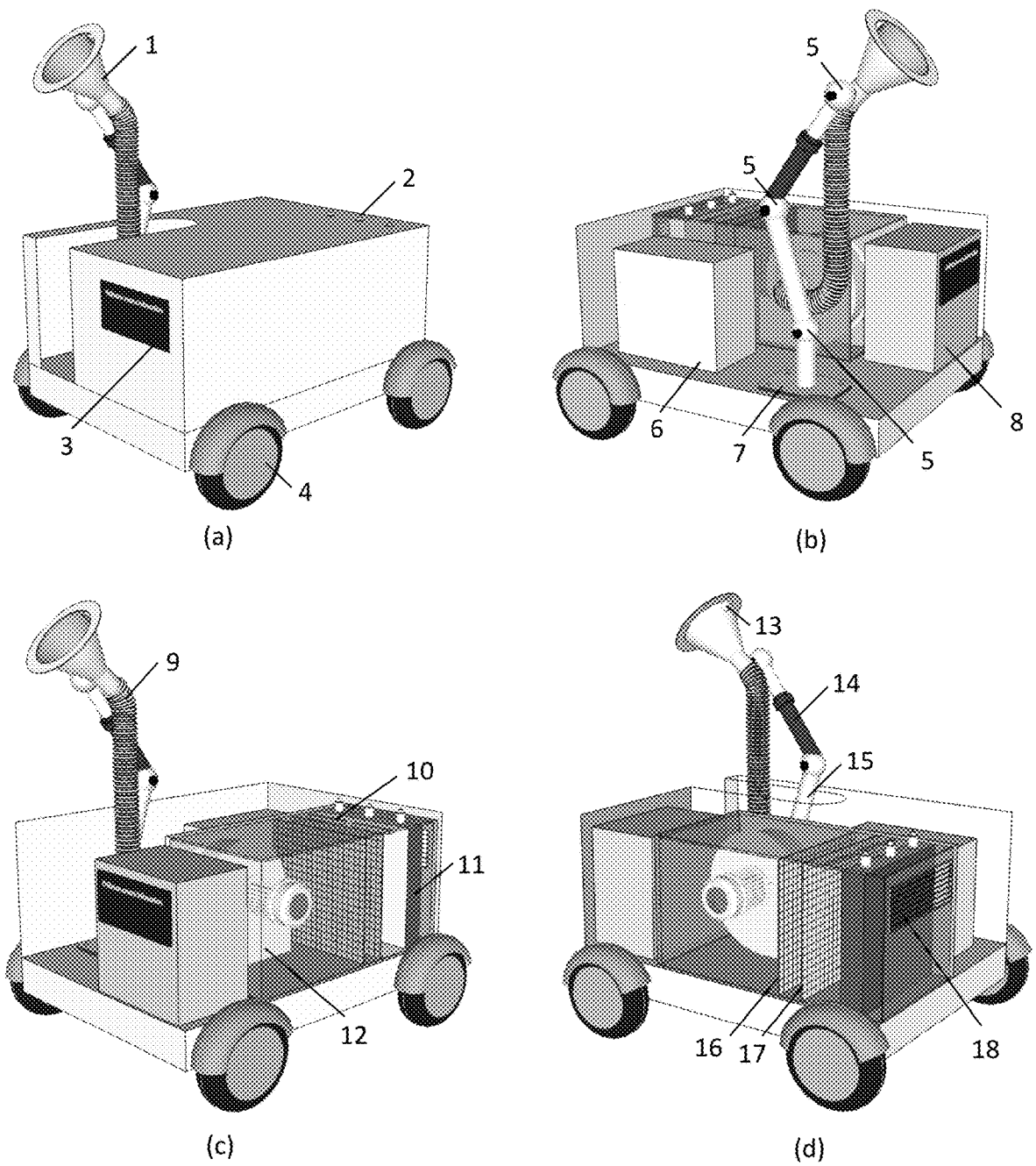
FIG. 1 is a schematic diagram of an automatic source-seeking indoor pollution purifying and removing device: (a) external; (b)-(d) internal side views from different angles.

The pollution source intelligent positioning and removing device provided by the present invention is described below in detail in combination with accompanying drawings and the technical solution. FIG. 1 is a schematic diagram of the device, comprising pollutant concentration sensors 2; a control unit 8; a position sensor 13; a power plant 6; a moving mechanism 4; a telescopic device: gimbals 5, a pollutant collection hood 7, a telescopic sleeve pipe 14 and a multi-section arm 15; a pollutant collection hood 1; and a filtering and purifying device: ultraviolet lamps 10, an activated carbon filter screen 11, a centrifugal fan 12, a primary filter screen 16, a high-efficiency filter screen 17 and an air outlet 18. The specific operation steps of the automatic source-seeking indoor pollution purifying and removing device are as follows:

Step 1, pre-inputting indoor geometric layout information and position information of all potential pollution sources indoors to the control unit according to the indoor environment where the device is located.

Step 2, assuming that x ($x \geq 1$) different kinds of potential pollution sources exist in a room, and the number of pollution sources of each kind is $n_p$ ($n_p \geq 1$; the subscript p represents the $p^{th}$ kind of pollution sources, and p=1, ..., x); inputting the set concentration alarm values $O_p$ of various kinds of pollutants to the control unit; arranging ($n_p-1$) wireless concentration sensors of each kind and a total of $$\sum_{p=1}^{x}(n_p - 1)$$

pollutant concentration sensors at any different positions in the room to monitor the concentrations of various kinds of pollutants; and returning the real-time concentration data monitored by each sensor and the sensor installation positions to the control unit;

Step 3, obtaining an indoor flow field through numerical simulation by solving Navier-Stokes equations according to the pre-input indoor geometric layout information in the control unit, and on the basis of this flow field, solving a species transport equation through numerical simulation for various kinds of pollutants to obtain a unit pulse response $F_{t_k,i}^j$ (k=1, ..., $m_p$; and $m_p$ is the multiple of the entire monitoring time of the sensor relative to $\Delta T$) of all potential pollution sources at the positions of all sensors (a total of $n_p$ sensors, including the ($n_p-1$) sensors arranged in the room and the one in the device), i.e., the concentration monitored by the $j^{th}$ sensor at the time $t=k\Delta T$ ($\Delta T$ is the minimum time interval of the concentration that can be monitored by the sensor) when a pollutant is released in pulse form at the position of the $i^{th}$ pollution source.

Step 4, when the concentration data monitored by sensors that monitor the concentrations of a certain kind of pollutants is greater than the set concentration alarm values $O_p$, transferring the concentration data monitored by all the sensors that monitor the concentrations of this kind of pollutants to the control unit. The concentration vector $C=[c^1, \ldots, c^j, \ldots, c^{n_p}]^T$ (composed of the concentration data monitored by each sensor for the same kind of pollutants) is formed in the control unit, and the response matrix A is established in the following form:

$$A = \begin{bmatrix} A_1^1 & \cdots & A_i^1 & \cdots & A_{n_p}^1 \\ \vdots & \ddots & \ddots & \ddots & \vdots \\ A_1^j & \ddots & A_i^j & \ddots & A_{n_p}^j \\ \vdots & \ddots & \ddots & \ddots & \vdots \\ A_1^{n_p} & \cdots & A_i^{n_p} & \cdots & A_{n_p}^{n_p} \end{bmatrix} \quad (1)$$

Wherein each submatrix $A_i^j$ (i=1, ..., $n_p$, which represents the $i^{th}$ pollution source; j=1, ..., $n_p$, which represents the $j^{th}$ sensor; and the order of sensor j is consistent with the order of constructing the concentration vector C) is obtained through formula (2):

$$A_i^j = \begin{bmatrix} F_{t_0,i}^j & 0 & \cdots & \cdots & \cdots & 0 \\ F_{t_1,i}^j & F_{t_0,i}^j & 0 & \cdots & \cdots & 0 \\ \vdots & \ddots & \ddots & \ddots & \ddots & \vdots \\ F_{t_k,i}^j & F_{t_{k-1},i}^j & \cdots & F_{t_0,i}^j & \cdots & 0 \\ \vdots & \ddots & \ddots & \ddots & \ddots & \vdots \\ F_{t_{m-1},i}^j & F_{t_{m-2},i}^j & \cdots & F_{t_{m-k},i}^j & \cdots & F_{t_0,i}^j \end{bmatrix} \in R^{m_p \times m_p} \quad (2)$$

Then the control unit uses formula (3) to identify the hourly release rates of all potential pollution sources of the same kind:

$$Q = (A^T A + \lambda^2 L^T L)^{-1}(A^T C) \quad (3)$$

Wherein $Q=[q_1, \ldots, q_i, \ldots, q_{n_p}]^T$, and contains the hourly release rates of $n_p$ potential pollution sources; $\lambda$ is a regularization parameter, and the inflection point of the curve of the regularization term $\|LQ\|_2$ changing with the solution error term $\|AQ-C\|_2$ is taken as the value of $\lambda$. L is a regularization matrix, and the expression is as follows:

$$L = \begin{bmatrix} 1 & -2 & 1 & 0 & \cdots & \cdots & \cdots & 0 \\ 0 & 1 & -2 & 1 & \ddots & \ddots & \ddots & \vdots \\ \vdots & \ddots & \ddots & \ddots & \ddots & \ddots & \ddots & \vdots \\ \vdots & \ddots & \ddots & 1 & -2 & 1 & \ddots & \vdots \\ \vdots & \ddots & \ddots & \ddots & \ddots & \ddots & \ddots & 0 \\ 0 & \cdots & \cdots & \cdots & 0 & 1 & -2 & 1 \end{bmatrix} \in R^{(m_p n_p - 2) \times m_p n_p} \quad (4)$$

Finally, $q_1, \ldots, q_{n_p}$ are obtained according to the calculated hourly release rate Q in the control unit, the positions of the potential pollution sources with a release rate of 0 are excluded, and the positions and hourly release rates of actual pollution sources are determined. The pollution source identifying process is shown in FIG. 2. The method is suitable for the following specific situations:

(1) When the flow field changes, it is necessary to obtain an indoor flow field through numerical simulation by solving Navier-Stokes equations again, and construct the response matrix A again;

(2) The pollution source identifying method can only identify multiple pollution sources that release the same kind of pollutants in one calculation; if multiple kinds of pollution sources exist in the room at the same time, formula (3) must be recalculated every time a pollution source is identified.

(3) The pollution sources that can be identified by the pollution source identifying method are point sources, or part of the actual line sources, surface sources or volume sources that can be approximated to point sources.

Step 5, after identifying pollution sources, the control unit outputs the positions and hourly release rates of the pollution sources on a pollution source information display, and sets the movement track of the device for this time according to the pre-input indoor geometric layout information, the position information from the position sensor, and the positions of actually determined pollution sources: when all pollution sources release the same kind of pollutants, the control unit arranges the track according to the hourly release rate of each pollution source from higher to lower; when multiple kinds of pollutants are released from each pollution source, the control unit sorts according to the distance between each pollution source and the device, and selects the shortest track that includes all pollution sources.

Step 6, the control unit issues an instruction to the power plant 6 according to the movement track; after receiving the instruction, the power plant 6 controls the moving mechanism 4 to move according to the predetermined track and controls the gimbals 5 to move the pollutant collection hood 1 to the position of the first pollution source; the control unit continues to dynamically update the pollution source information according to the concentration data monitored by the pollutant concentration sensors in the process of device movement, and repeats step 5 when the pollution source information changes. The pollutant collection hood can collect pollutants at any position in the room; FIG. 3 is a schematic diagram of the pollutant collection hood 1 collecting pollutants at a relatively low pollution source; and FIG. 4 is a schematic diagram of the pollutant collection hood 1 collecting pollutants at a relatively high pollution source.

Step 7, after the pollutant collection hood is moved to a designated position, the power plant 6 stops working, the fan 12 starts running, and the pollutants at the position of a pollution source is sucked into the device; the pollutants successively passes through the primary filter screen 16 (where relatively large particulates are removed), the high-efficiency filter screen 17 (where PM2.5 are removed), the ultraviolet lamps 10 (where microorganisms are removed), and the activated carbon filter screen 11 (where VOCs are removed), and the processed air is sent back to the room through the air outlet 18; the control unit continues to dynamically update the pollution source information according to the concentration data monitored by the pollutant concentration sensors in the process of pollutant removal, and repeats steps 5 and 6 when the pollution source information changes.

Step 8, when the concentrations monitored by all the sensors that monitor the concentrations of this kind of pollutants are lower than the set pollutant concentration alarm values $O_p$, the fan 12 stops running, the power plant 6 starts running, and the device repeats steps 6-7 to make the pollutant collection hood 1 move to the position of a next identified pollution source according to the set track and conduct pollutant collection and removal.

Step 9, when the concentrations monitored by all the pollutant concentration sensors are lower than the alarm values, the fan 12 stops running, the power plant 6 starts running, and the device returns to the original position along the original route, i.e., one indoor pollution purification and removal is completed.

The invention claimed is:

1. An automatic source-seeking indoor pollution purifying and removing device, comprising pollutant concentration sensors, a control unit, a position sensor, a power plant, a moving mechanism, a telescopic device, a pollutant collection hood, and a filtering and purifying device; the pollutant concentration sensors are used to monitor indoor pollutant concentration and transfer data to the control unit; the control unit is used to identify actual pollution source information of relevant pollutants according to concentration data monitored by the pollutant concentration sensors, and issue a movement instruction to the power plant according to a current position signal sent by the position sensor in the device; the actual pollution source information includes the release positions of pollutants; the power plant is used to move the pollutant collection hood to the positions of identified pollution sources by controlling the moving mechanism and the telescopic device; the pollutants collected by the pollutant collection hood are sucked into the filtering and purifying device through a fan for removal; and the inside of the power plant is provided with power supply equipment to supply power for the moving mechanism, the telescopic device and the fan.

2. The automatic source-seeking indoor pollution purifying and removing device of claim 1, wherein the control unit identifies the actual pollution source information of relevant pollutants according to positions of potential pollution sources of relevant pollutants in combination with the concentration data monitored by the pollutant concentration sensors; the control unit also continues to dynamically update the pollution source information according to the concentration data monitored by the pollutant concentration sensors in the process of device movement or pollutant removal, until the pollutant concentrations at the positions of all pollution sources are lower than corresponding pollutant concentration alarm values; and the actual pollution source information also includes the hourly release rates of pollution sources.

3. The automatic source-seeking indoor pollution purifying and removing device of claim 1, wherein after identifying pollution sources, the control unit arranges a movement track of the device according to pre-input indoor geometric layout information; a front part of the moving mechanism is provided with an obstacle monitoring sensor which returns a signal to the control unit to correct the movement track when an obstacle is encountered; and the control unit also internally has an automatic return function which enables the device to return to an original position after all pollution sources are removed.

4. The automatic source-seeking indoor pollution purifying and removing device of claim 3, wherein the movement track of the device arranged according to the pre-input indoor geometric layout information is that: when all pollution sources release same kind of pollutants, the control unit arranges the track according to an hourly release rate of each pollution source from higher to lower, and then issues a movement instruction to the power plant; when multiple kinds of pollutants are released from each pollution source, the control unit sorts according to a distance between each pollution source and the device, selects a shortest track that includes all pollution sources, and then issues an instruction to the power plant.

5. The automatic source-seeking indoor pollution purifying and removing device of claim 1, wherein the pollutant concentration sensors comprise a VOC sensor, a microbial sensor and a particulate sensor to monitor the concentrations of indoor pollutants in real time.

6. The automatic source-seeking indoor pollution purifying and removing device of claim 1, wherein the inside of the control unit is provided with a module for controlling the start and stop of the fan; when the pollutant collection hood moves to a release position where a pollution source is located, the fan starts running; and when the concentrations monitored by all the pollutant concentration sensors are lower than a corresponding pollutant concentration alarm values, the fan stops running.

7. The automatic source-seeking indoor pollution purifying and removing device of claim 1, wherein the moving mechanism is connected with the power supply equipment in the power plant, and receives the movement instruction issued by the power plant.

8. The automatic source-seeking indoor pollution purifying and removing device of claim 1, wherein the telescopic device comprises a fixed base, gimbals and a multi-section arm; the telescopic device is fixed in the device through the fixed base; the pollutant collection hood is connected with the multi-section arm through the gimbals, the multi-section arm closest to the pollutant collection hood is a telescopic sleeve pipe, and a length of the multi-section arm can be adjusted to change the position of the pollutant collection hood; and each gimbal is connected with the power supply equipment in the power plant, and receives the movement instruction issued by the power plant.

9. The automatic source-seeking indoor pollution purifying and removing device of claim 1, wherein the inside of the filtering and purifying device is sequentially provided with a primary filter screen, a high-efficiency filter screen, ultraviolet lamps, activated carbon and an air outlet, so as to purify multiple kinds of pollutants and discharge the purified air through the air outlet.

10. A pollution source identifying method of the automatic source-seeking indoor pollution purifying and removing device of claim 1, comprising the following identifying process:
   (1) pre-inputting indoor geometric layout information and position information of potential pollution sources indoors to the control unit;
   (2) arranging n-1 sensors that monitor the concentrations of a same kind of pollutants at any different positions in a room according to a number n ($n \geq 1$) of potential pollution sources for various kinds of pollutants, and returning a real-time concentration data monitored by each sensor and sensor installation positions to the control unit; and
   (3) obtaining an indoor flow field through numerical simulation by solving Navier-Stokes equations according to the pre-input indoor geometric layout information in the control unit, and on the basis of this flow field, solving a species transport equation through numerical simulation for various kinds of pollutants to obtain a unit pulse response F of all potential pollution sources at the positions of the n-1 sensors, so as to identify the positions and hourly release rates of actual pollution sources for various kinds of pollutants.

* * * * *